US 10,513,991 B2

(12) United States Patent
Murakami et al.

(10) Patent No.: US 10,513,991 B2
(45) Date of Patent: Dec. 24, 2019

(54) FUEL PROPERTY DETERMINING DEVICE AND COMBUSTION CONTROL DEVICE FOR ENGINE

(71) Applicant: Mazda Motor Corporation, Aki-gun, Hiroshima (JP)

(72) Inventors: Takuya Murakami, Aki-gun (JP); Tetsuhide Kanda, Hiroshima (JP)

(73) Assignee: Mazda Motor Corporation, Aki-gun, Hiroshima (JP)

( * ) Notice: Subject to any disclaimer, the term of this patent is extended or adjusted under 35 U.S.C. 154(b) by 268 days.

(21) Appl. No.: 15/658,710

(22) Filed: Jul. 25, 2017

(65) Prior Publication Data

US 2018/0058349 A1    Mar. 1, 2018

(30) Foreign Application Priority Data

Aug. 26, 2016 (JP) ................. 2016-165480

(51) Int. Cl.
| | |
|---|---|
| F02D 35/00 | (2006.01) |
| F02D 41/00 | (2006.01) |
| G01M 15/04 | (2006.01) |
| G01N 33/28 | (2006.01) |
| G01M 15/11 | (2006.01) |

(52) U.S. Cl.
CPC ....... *F02D 35/0007* (2013.01); *F02D 41/005* (2013.01); *G01M 15/046* (2013.01); *G01N 33/2829* (2013.01); *F02D 2200/0611* (2013.01); *G01M 15/11* (2013.01)

(58) Field of Classification Search
CPC ............... F02D 35/0007; F02D 41/401; F02D 41/0002; F02D 41/08; F02D 41/005; F02D 2200/1012; F02D 2200/0611; G01N 33/2829; G01M 15/046; G01M 15/11; Y02T 10/44; Y02T 10/42; Y02T 10/47

See application file for complete search history.

(56) References Cited

U.S. PATENT DOCUMENTS

| | | | | |
|---|---|---|---|---|
| 7,926,331 | B2 * | 4/2011 | Tsutsumi ............ | F02D 41/0025 73/114.38 |
| 8,423,267 | B2 * | 4/2013 | Iwatani ................. | F02D 41/401 123/406.3 |
| 8,850,877 | B2 * | 10/2014 | Inuzuka ................ | F01N 11/007 73/114.74 |
| 9,127,608 | B2 * | 9/2015 | Ito ....................... | F02D 41/1497 |
| 9,423,390 | B2 * | 8/2016 | Tsuchiyama .......... | F02D 19/061 |
| 9,556,845 | B2 * | 1/2017 | Sasaki ................... | F02D 41/064 |

(Continued)

FOREIGN PATENT DOCUMENTS

| | | |
|---|---|---|
| JP | 11050902 A | 2/1999 |
| JP | 3626020 B2 | 3/2005 |

(Continued)

*Primary Examiner* — Freddie Kirkland, III
(74) *Attorney, Agent, or Firm* — Alleman Hall Creasman & Tuttle LLP

(57) ABSTRACT

A fuel property determining device for an engine is provided, the device retarding a fuel injection timing and determining a fuel property based on a combustion variation of the engine caused by the retarding. The device includes a processor configured to control a parameter related to combustibility so as to degrade a combustion state before the fuel injection timing is retarded, the parameter being different from the fuel injection timing.

7 Claims, 4 Drawing Sheets

(56) References Cited

U.S. PATENT DOCUMENTS

| | | | |
|---|---|---|---|
| 2007/0151542 A1* | 7/2007 | Yamaguchi | F02D 35/023 123/299 |
| 2009/0198456 A1* | 8/2009 | Tsutsumi | F02D 41/0025 702/41 |
| 2010/0191440 A1* | 7/2010 | Iwatani | F02D 41/401 701/103 |
| 2013/0000606 A1* | 1/2013 | Watanabe | F02D 41/402 123/478 |
| 2016/0010580 A1* | 1/2016 | Yamamoto | F02D 41/1461 73/53.01 |

FOREIGN PATENT DOCUMENTS

| | | |
|---|---|---|
| JP | 2007154699 A | 6/2007 |
| JP | 2007332877 A | 12/2007 |
| JP | 2009036027 A | 2/2009 |

* cited by examiner

FUEL PROPERTY DETERMINING DEVICE AND COMBUSTION CONTROL DEVICE FOR ENGINE

BACKGROUND

The present disclosure relates to a fuel property determining device and a combustion control device for an engine.

While a fuel property greatly influences combustibility (e.g., ignitability) of engines, the fuel property may significantly vary depending on the production area of the fuel, etc. Therefore, if the fuel property changes while a combustion control amount of the engine is constant, the combustibility greatly changes. JP2009-036027A discloses an art for retarding a fuel injection timing and detecting (determining) a cetane number as a fuel property based on the combustion state (misfire/ignition) when the retarded timing is applied.

If the retarding of the fuel injection timing for the fuel property determination is performed when the combustion state (combustibility) is good, since only a slight combustion variation occurs, it is difficult to accurately determine the fuel property. For example, in a case of retarding the fuel injection timing when the engine is idling so as to determine the fuel property, since the combustion state during idling changes depending on the environment, etc., the combustion variation is large at times and small at other times even with the same retarding amount of the fuel injection timing. This causes difficulty in determining the fuel property (degrade the determination accuracy). Note that although it may be considered to perform the determination only when the combustion state is within a given range, the frequency of the determination decreases in this case.

SUMMARY

The present disclosure is made in view of the above issues and aims to provide a fuel property determining device for an engine, which is capable of accurately determining a fuel property and increasing a frequency of the determination.

The present disclosure also aims to provide a combustion control device for an engine, which suitably executes a combustion control of the engine depending on a fuel property.

According to one aspect of the present disclosure, a fuel property determining device for an engine is provided, the device retarding a fuel injection timing and determining a fuel property based on a combustion variation of the engine caused by the retarding. The device includes a processor configured to control a parameter related to combustibility so as to degrade a combustion state before the fuel injection timing is retarded, the parameter being different from the fuel injection timing.

According to this configuration, the fuel injection timing is retarded in a state where the combustion state is degraded. Therefore, a great combustion variation is caused accompanying the retarding and the fuel property is determined with high precision. Further, even when the combustion state is high (good), a frequency of determining the fuel property is increased by degrading the combustion state.

The combustion state may be degraded by increasing an exhaust gas recirculation (EGR) amount before retarding the fuel injection timing. In this case, the combustion state is degraded by a simple approach of increasing an EGR amount (that is, reducing an oxygen concentration within a cylinder of the engine).

An intake air pressure may be reduced by narrowing an opening of a throttle valve before retarding the fuel injection timing. In this case, the combustion state is degraded by a simple approach of reducing the intake air pressure by narrowing the opening of the throttle valve.

The fuel injection timing may be retarded under a condition in which the intake air pressure is brought into a given range by controlling the throttle valve. This configuration is advantageous in determining the fuel property with high precision by bringing the intake air pressure into the given range to have a stable combustion state which is a degraded state.

An external load on the engine may be reduced before retarding the fuel injection timing. This configuration is advantageous in determining the fuel property with high precision by preventing a combustion variation based on a variation in the external load.

The combustion state may be degraded after the combustion state becomes stable. This configuration is advantageous in determining the fuel property with high precision.

The fuel property may be determined when the engine is idling. This configuration is advantageous in sufficiently securing the determination frequency of the fuel property. Further, this configuration is advantageous in increasing the determination accuracy by determining the fuel property in the idling operation during which the engine speed is substantially fixed.

The combustion variation may be a variation in an engine speed when the fuel injection timing is retarded. This configuration is advantageous in easily detecting the combustion variation.

A cetane number may be determined as the fuel property. In this case, the cetane number which greatly influences ignitability is determined.

According to another aspect of the present disclosure, a combustion control device for an engine is provided, the device retarding a fuel injection timing when a given operation condition is satisfied, and determining a combustion control amount of the engine in a normal operating state based on a combustion variation of the engine caused by the retarding. The device includes a processor configured to control a parameter related to combustibility so as to degrade a combustion state before the fuel injection timing is retarded, the parameter being different from the fuel injection timing. According to this configuration, the combustion control amount is suitably set depending on a difference in a fuel property, and it is also advantageous in securing a sufficient frequency of setting the combustion control amount.

In the given operation condition, the engine may be idling. This configuration is advantageous in sufficiently securing the frequency of setting the combustion control amount. Further, this is also advantageous in more suitably setting the combustion control amount since the setting is based on the combustion control amount in the idling operation during which the engine speed is substantially fixed.

The combustion control amount of the engine may be the fuel injection timing.

DETAILED DESCRIPTION OF EMBODIMENT

Figure 1:
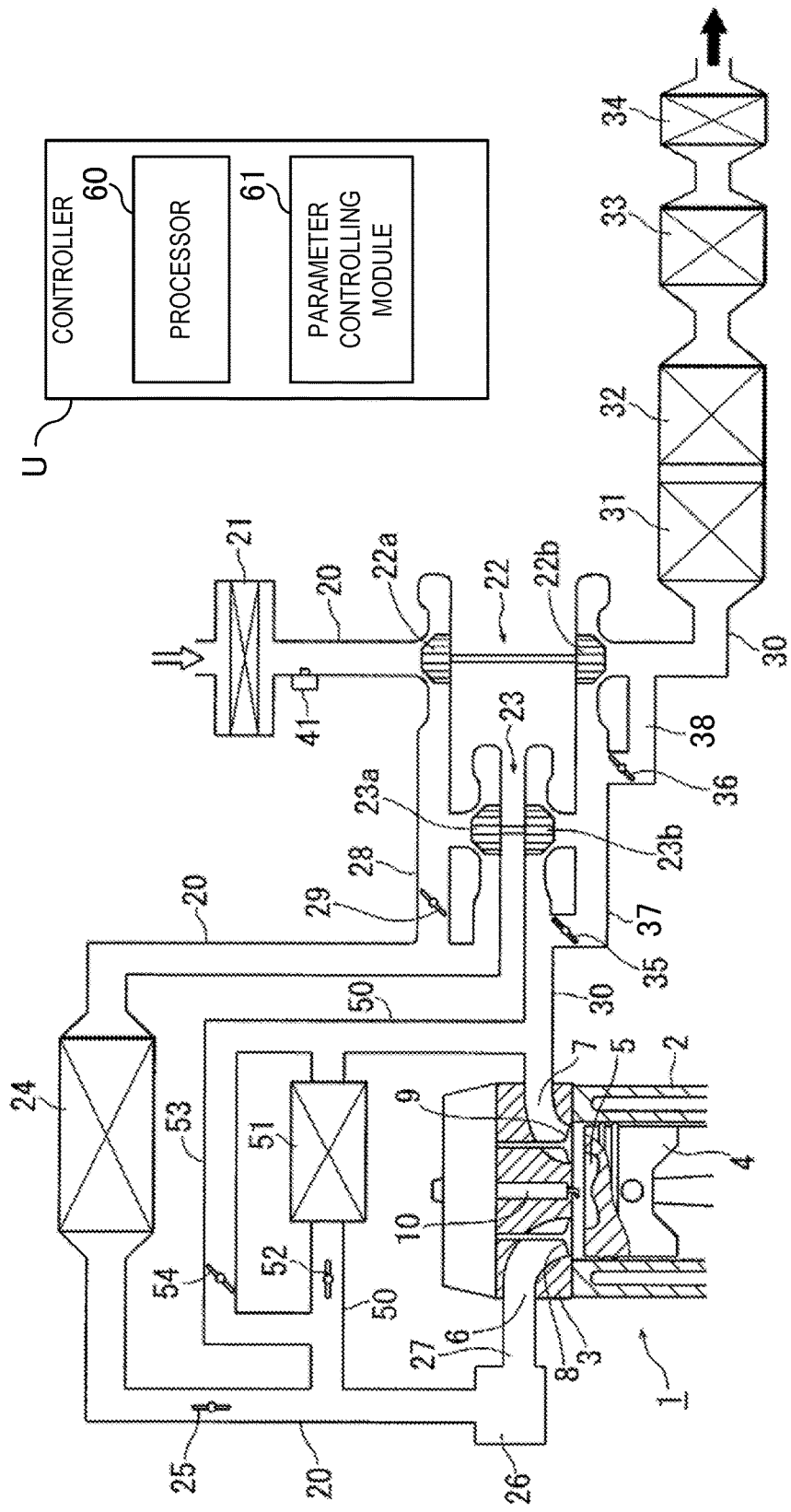
FIG. 1 is a view illustrating one example of an engine to which the present disclosure is applied.

In FIG. 1, "1" is an engine (engine body) and, in one embodiment, is an inline four-cylinder diesel engine for an automobile. As is known, the engine 1 has cylinders 2, a cylinder head 3, and pistons 4. An intake port 6 and an exhaust port 7 open to a combustion chamber 5 formed above each piston 4. The intake port 6 is opened and closed by an intake valve 8, and the exhaust port 7 is opened and closed by an exhaust valve 9. Fuel injectors 10 are attached to the cylinder head 3 so as to face the combustion chambers 5, respectively. In this embodiment, the fuel injection is a common rail type in which fuel is injected at an extremely high pressure by each fuel injector 10.

In an intake passage 20 connected to the intake ports 6, an air cleaner 21, a compressor wheel 22a of a first exhaust turbocharger 22, a compressor wheel 23a of a second exhaust turbocharger 23, an intercooler 24, a throttle valve 25, and a surge tank 26 are disposed in this order from an upstream side. The surge tank 26 is connected to (the intake ports 6 of) the cylinders by branched intake passages 27, respectively.

The intake passage 20 is provided with a bypass passage 28. An upstream end of the bypass passage 28 opens to the intake passage 20 between the compressor wheels 22a and 23a. A downstream end of the bypass passage 28 opens to the intake passage 20 between the compressor wheel 23a and the intercooler 24. A control valve 29 is disposed in the bypass passage 28.

In an exhaust passage 30 connected to the exhaust ports 7, a turbine wheel 23b of the second exhaust turbocharger 23, a turbine wheel 22b of the first exhaust turbocharger 22, an oxidation/$NO_x$ catalyst 31, a diesel particulate filter (DPF) 32, a urea catalyst 33, and an ammonia processor 34 are disposed in this order from an upstream side.

The exhaust passage 30 has a bypass passage 37 and a wastegate passage 38. An upstream end of the bypass passage 37 opens to the exhaust passage 30 upstream of the turbine wheel 23b. A downstream end of the bypass passage 37 opens to the exhaust passage 30 between the turbine wheels 22b and 23b. A control valve 35 for controlling a flow rate of exhaust gas is disposed in the bypass passage 37.

An upstream end of the wastegate passage 38 opens to the exhaust passage 30 between the turbine wheels 22b and 23b. A downstream end of the wastegate passage 38 opens to the exhaust passage 30 between the turbine wheel 22b and the catalyst 31. A wastegate valve 36 for controlling a flow rate of the exhaust gas is disposed in the wastegate passage 38.

The intake passage 20 and the exhaust passage 30 are connected to each other via an EGR passage 50. An upstream end of the EGR passage 50 opens to the exhaust passage 30 upstream of the turbine wheel 23b. A downstream end of the EGR passage 50 opens to the intake passage 20 between the throttle valve 25 and the surge tank 26.

An EGR cooler 51 is connected to the EGR passage 50 and an EGR valve 52 is disposed in the EGR passage 50 downstream of the EGR cooler 51. The EGR passage 50 is provided with a bypass passage 53 for bypassing the EGR cooler 51. An upstream end of the bypass passage 53 opens to the EGR passage 50 upstream of the EGR cooler 51 and a downstream end thereof opens to the EGR passage 50 downstream of the EGR valve 52. A control valve 54 is disposed in the bypass passage 53.

The first exhaust turbocharger 22 is larger in size than the second exhaust turbocharger 23. Within an engine operating range where an engine speed and an engine load are low, turbocharging is performed mainly by the smaller second exhaust turbocharger 23, and the control valves 29 and 35 are closed at this time. Within an engine operating range where the engine load is high, turbocharging is performed mainly by the larger exhaust turbocharger 22, and the control valves 29 and 35 are opened at this time. The wastegate valve 36 is opened when the turbocharging pressure exceeds a given upper limit pressure.

Further included in FIG. 1 is a controller U for the engine 1, which may include a processor 60 and memory configured to store various instructions. The processor 60 may be configured to execute a parameter controlling module 61, which is a software module stored in the memory, in order to perform its associated function.

Figure 2:
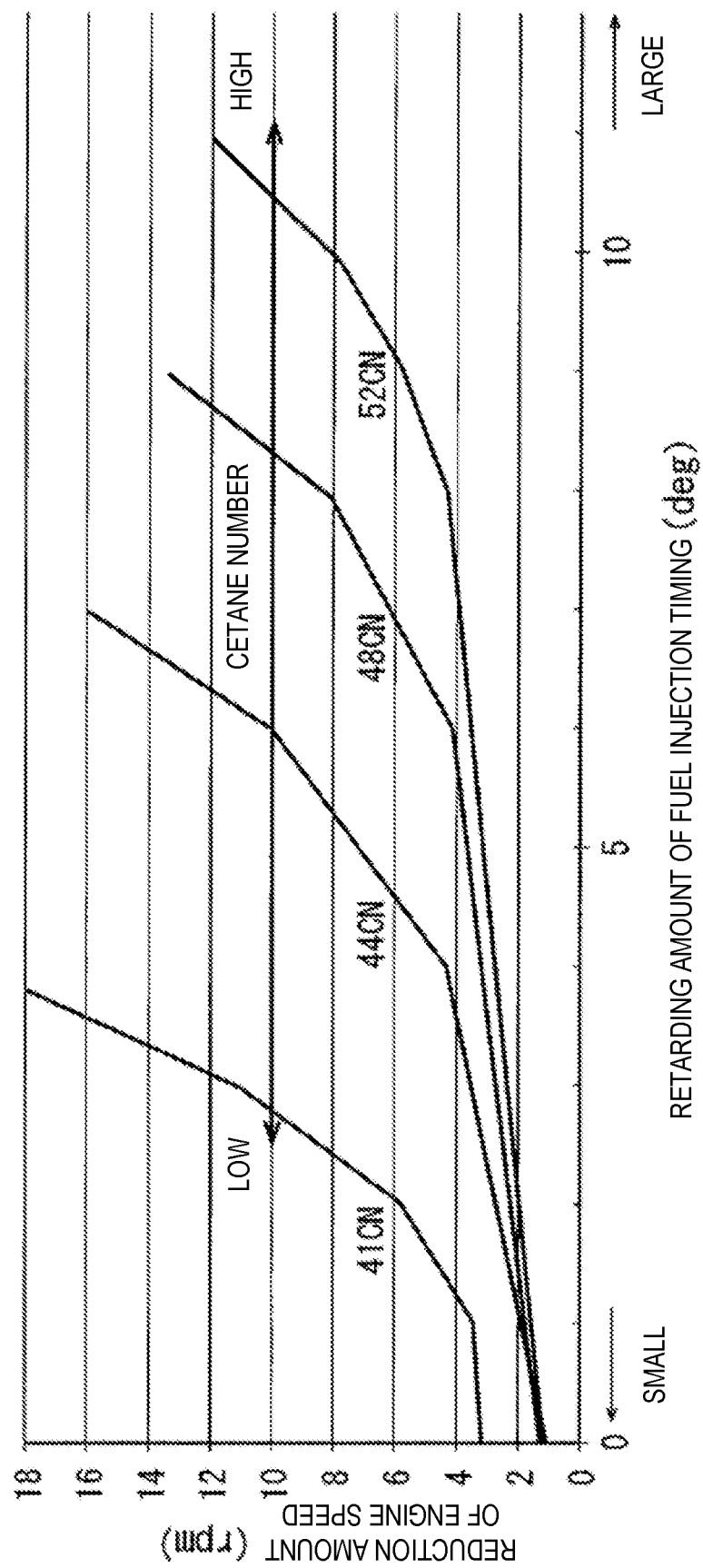
FIG. 2 is a chart illustrating a relationship of a cetane number of fuel, a retarding amount of a fuel injection timing, and a reduction amount of an engine speed.

Next, a relationship between a cetane number as a fuel property, a retarding amount of a fuel injection timing, and a reduction amount of the engine speed is described with reference to FIG. 2. Note that FIG. 2 is based on the engine 1 in an idle operation.

First, the retarding amount of the fuel injection timing for a fuel property determination is desirably set within a range where a misfire of the engine 1 does not occur (e.g., the reduction amount of the engine speed is 12 rpm or below) but the reduction of the engine speed is clearly recognizable (e.g., 6 rpm or above).

Here, a case where the cetane number as the fuel property is determined in two stages by having 44 CN as a threshold is described. If the cetane number of currently used fuel is about 44 CN, by retarding the fuel injection timing by, for example, 5 degrees, the reduction amount of the engine speed is within the given range (e.g., 6 rpm to 12 rpm), and thus, it is determined that the cetane number is 44 CN or below.

On the other hand, in a case where the cetane number of the currently used fuel is about 41 CN, if the fuel injection timing is retarded by 5 degrees, the engine speed drops extremely sharply, e.g., by several tens of rpm, causing a misfire or an engine stop. Thus, it is difficult to retard by 5 degrees. Therefore, when the cetane number is about 41 CN, the retarding amount of the fuel injection timing needs to be set to a considerably small value, such as around 2.5 degrees.

Note that in the above description, the case where the determination is performed based on whether the cetane number is larger than 44 CN which is the threshold is described; however, a similar manner of the determination may be adopted even if, for example, when 48 CN is used as a threshold. Further, the cetane number may be determined based on the reduction amount of the engine speed which corresponds to the retarding amount of the fuel injection timing. In either case, when the cetane number is small, the retarding amount of the fuel injection timing needs to be reduced smaller than when the cetane number is large.

Next, the control contents of this embodiment of the present disclosure are described with reference to the time chart of FIG. 3. First, the determination of the fuel property is made when idling and in a state where combustion is sufficiently stable (until time t1 in FIG. 3 is a preparation period for determination).

Figure 3:
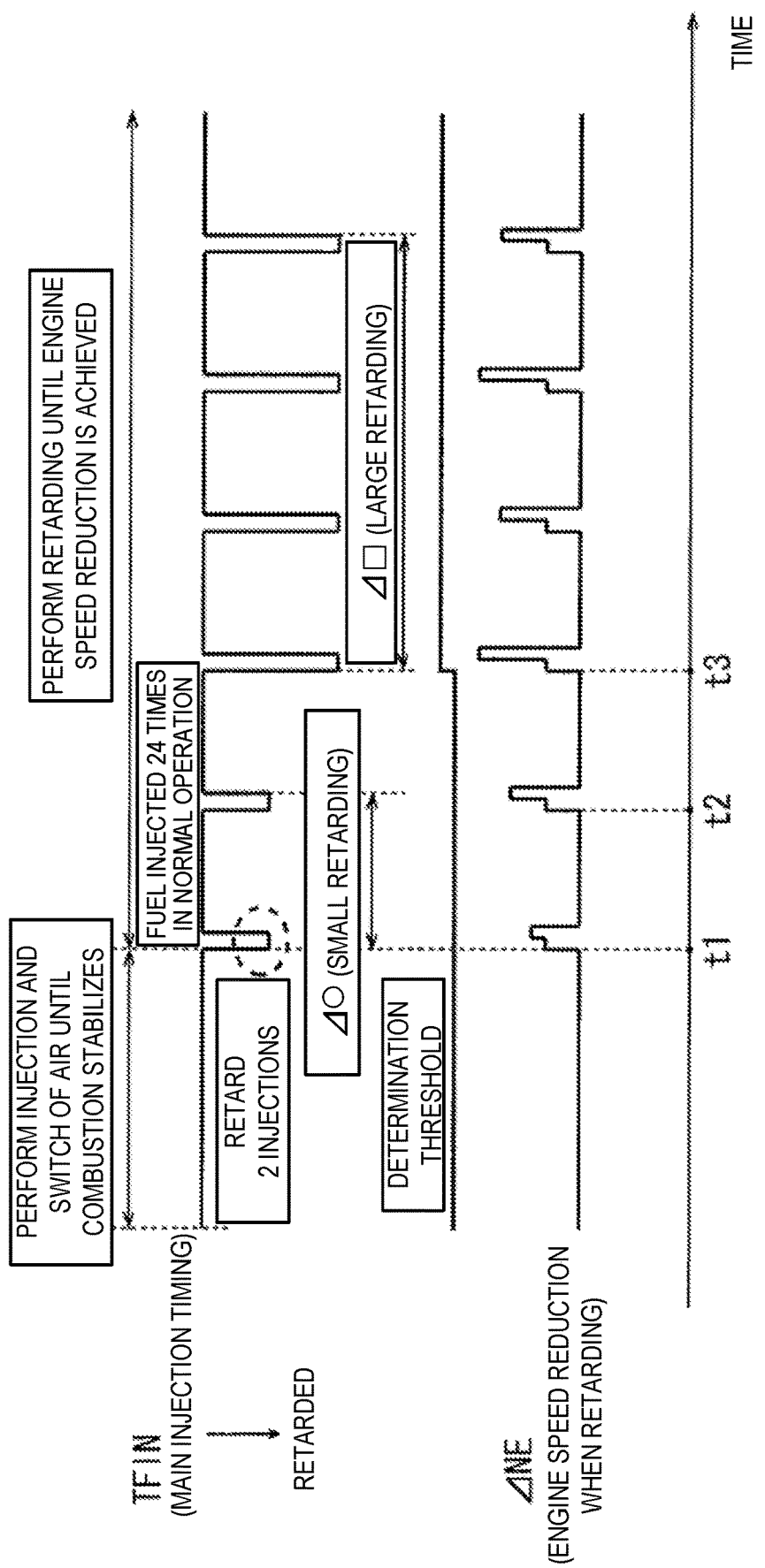
FIG. 3 is a time chart illustrating a relationship between a situation where the fuel injection timing is retarded and the reduction of the engine speed.

The control from time t1 to time t2 in FIG. 3 corresponds to an early stage of the fuel property determination. That is, at the early stage, the retarding amount of the fuel injection timing is set small for the case where the cetane number of the currently used fuel is considerably small. The retarding amount at the early stage is a first setting amount, which is the value indicated by triangle and circle marks in FIG. 3 (e.g., 2.5 degrees). With the small retarding amount at the early stage, whether the reduction amount of the engine speed is above a first given value (e.g., 6 rpm or above) is determined. When the reduction amount of the engine speed is above the first given value, the cetane number is determined to be below the given value, and the fuel injection timing is not retarded thereafter. Since the cetane number is determined to be small, the fuel injection timing in a normal operation is advanced.

The small retarding of the fuel injection timing at the early stage of the determination is performed from time t1 for specific two of the cylinders of which fuel injection timing is adjacent among the four cylinders (hereinafter, these two cylinders may be referred to as "first cylinder" and "third cylinder"), then the retarding is suspended for a given suspension period (e.g., period corresponding to fuel injected 24 times), and at time t2 which is after the suspension period, the retarding is performed for the other two cylinders (hereinafter, these two cylinders may be referred to as "second cylinder" and "fourth cylinder"). The retarding is suspended so as to reliably avoid a problem such as the misfire, due to retarding continuously. Further, the retarding is performed depending on the cylinder so as to also take into consideration a difference in combustibility of each cylinder.

If the reduction amount of the engine speed is small due to the retarding of the fuel injection timing at the early stage (e.g., below 6 rpm), the fuel injection timing is retarded larger at time t3 to start a later stage of the determination. The retarding amount of the fuel injection timing at the later stage of the determination is a second setting amount, which is the value indicated by triangle and square marks in FIG. 3. The threshold for the reduction amount of the engine speed at the later stage of the determination may be set equal to or larger than the first given value at the early stage of the determination (e.g., 8 rpm).

The large retarding amount of the fuel injection timing at the later stage of the determination is performed for the first and third cylinders, then the retarding is suspended for a given suspension period (e.g., period corresponding to fuel injected 24 times), and then, the retarding is performed for the second and fourth cylinders. The retarding is suspended so as to reliably avoid the problem such as the misfire, due to retarding continuously. Further, the retarding is performed depending on the cylinder so as to also take into consideration a difference in combustibility of each cylinder.

The number of times that the fuel injection timing is retarded in the later stage of the determination is made larger than that at the early stage of the determination (in this embodiment, twice the number of times of the retarding at the early stage of the determination). Further, the determination period from the start to the end of the retarding the fuel injection timing is made longer than the determination period at the early stage of the determination. By increasing the number of times of the retarding or extending the determination period as described above, the fuel property is determined more accurately.

When the reduction amount of the engine speed is above a second given value due to the later stage of the determination, the cetane number is determined to be below a given threshold. Based on the determination that the cetane number is small, the fuel injection timing in the normal operation is advanced. When the reduction amount of the engine speed is below the second given value, the cetane number is determined to be above the given threshold. Based on the determination that the cetane number is large, the fuel injection timing in the normal operation is retarded more than when the cetane number is determined to be small.

Figure 4:
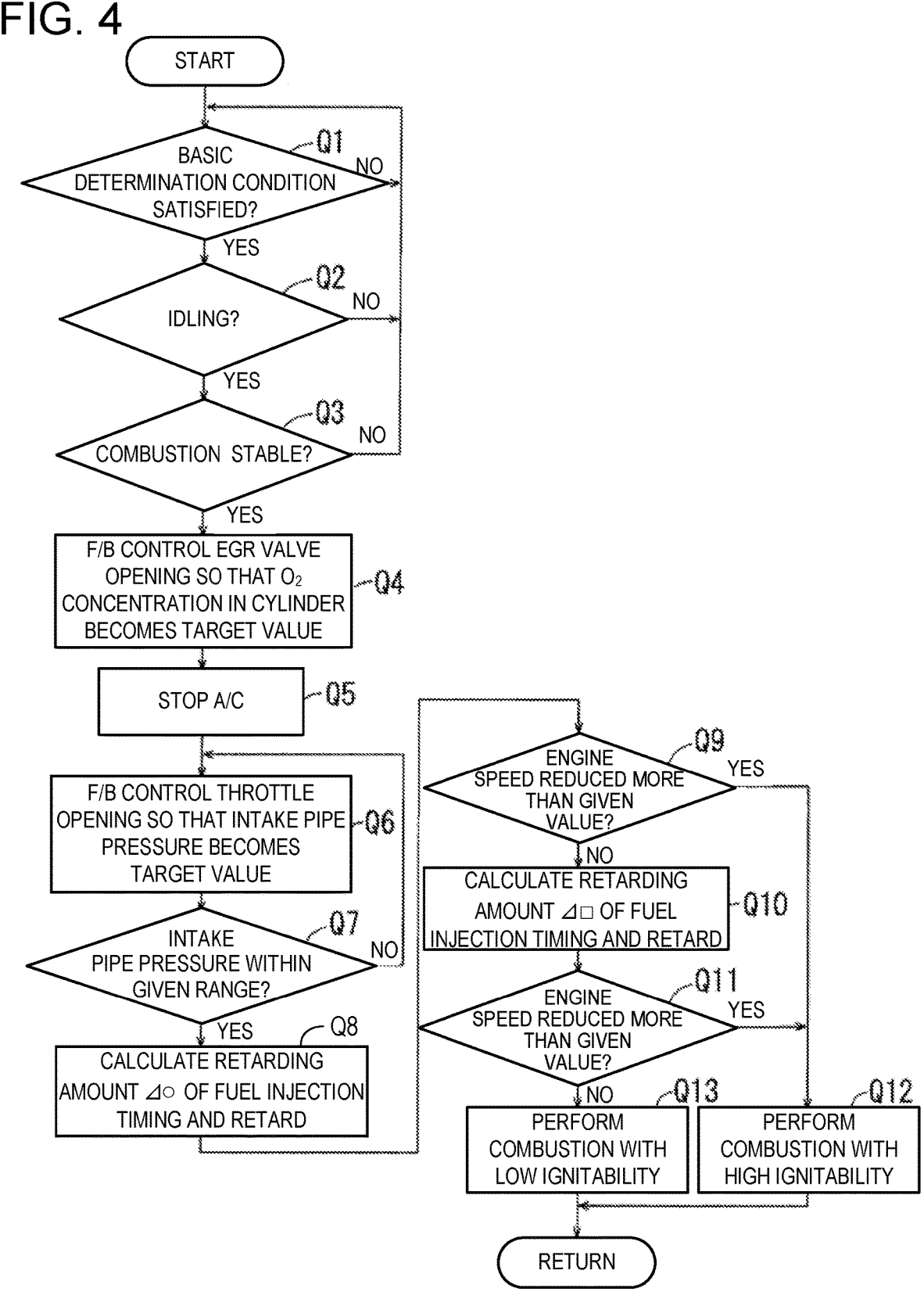
FIG. 4 is a flowchart illustrating a control example of the present disclosure.

Next, a control example of this embodiment of the present disclosure is described with reference to the flowchart of FIG. 4. In the following description, "Q" indicates a step. Further, the control details illustrated in FIG. 4 are of the controller U for the engine control, which is illustrated in FIG. 1. Note that the input-output relationship of various sensors and devices with the controller U is described when the flowchart is explained.

First, at Q1, whether a basic determination condition is satisfied is determined. This determination is for eliminating a severe environmental condition for combustion, for example, whether a coolant temperature, an intake air temperature, an atmospheric pressure, and an atmospheric temperature which are inputted to the controller U from the various sensors, are within given ranges is determined. If the determination at Q1 is NO, the environment is determined to be not suitable for the determination of the fuel property, and the process returns to Q1.

If the determination at Q1 is YES, at Q2, whether the engine is idling is determined (e.g., based on the engine speed and a vehicle speed inputted to the controller U). If the determination at Q2 is NO, the process returns to Q1. If the determination at Q2 is YES, at Q3, whether the combustion is stable is determined. In this embodiment, the determination at Q3 is a determination of whether a variation amount of the engine speed when idling is within a given range (e.g., 4 rpm or below).

If the determination at Q3 is NO, the process returns to Q1. If the determination at Q3 is YES, at Q4, an opening of the EGR valve 52 is feedback-controlled so that an oxygen concentration within the cylinder becomes a target value (e.g., 15%) which is lower than that in the normal operation. For the control at Q4, the controller U receives a signal from an intake air amount sensor 41 provided in the intake passage 20. Note that the target value is changed according to the environment.

Then at Q5, operation of an air conditioner is stopped to fix the operation state of the air conditioner. Thus, a variation in the external load on the engine by a change in the operation state of the air conditioner is prevented.

Then at Q6, an opening of the throttle valve 25 is feedback-controlled so that an intake pipe pressure becomes a target value which is lower than that in the normal operation. Note that the controller U receives a signal from an intake air pressure sensor (not illustrated). The target value is changed according to the environment. Then, at Q7, whether the intake pipe pressure is within a given range is determined. If the determination at Q7 is NO, the process returns to Q6. Note that the processes at Q4 and Q6 are for facilitating the reduction of the engine speed by degrading the combustion state (combustibility) and retarding the fuel injection timing.

If the determination at Q7 is YES, the determination of the fuel property by retarding the fuel injection timing, and the setting of the fuel injection timing (combustion control amount) for the normal operation based on the determination result are performed. That is, first at Q8, the retarding amount of the fuel injection timing is set to the small first setting amount, which corresponds to the early stage of the determination. Note that the first setting amount is set (corrected) based on a gear range of a transmission (transmission resistance) and the fuel injection amount.

Then at Q9, whether the reduction amount of the engine speed is above the first given value is determined. If the determination at Q9 is YES, at Q12, the fuel property is determined to be poor (the cetane number is below the given value) and the fuel injection timing in the normal operation is advanced.

If the determination at Q9 is NO, the later stage of the determination from Q10 is performed. That is, at Q10, the retarding amount of the fuel injection timing is set to the large second setting amount. Note that the second setting amount is set (corrected) based on the gear range of the transmission (transmission resistance) and the fuel injection amount. Then at Q11, whether the reduction amount of the engine speed is above the second given value is determined. If the determination at Q11 is YES, the process proceeds to Q12.

If the determination at Q11 is NO, at Q13, the fuel property is determined to be good (the cetane number is above the given threshold) and the fuel injection timing in the normal operation is retarded.

Here, the processes at Q4 and Q6 are for facilitating the reduction of the engine speed by degrading the combustion state (combustibility) and retarding the fuel injection timing. That is, when the oxygen concentration within the cylinder is high or the intake pipe pressure is high (i.e., the combustion state is good (high combustibility)), the reduction amount of the engine speed with respect to the retarding amount of the fuel injection timing becomes small, and the determination accuracy of the fuel property degrades. Therefore, by degrading the combustion state before retarding the fuel injection timing, the reduction amount of the engine speed with respect to the retarding amount of the fuel injection timing is increased (the increase rate of the reduction amount of the engine speed with respect to the increase of the retarding amount rises) and the determination accuracy of the fuel property improves. Note that the property illustrated in FIG. 3 is for the state where the combustion state is degraded (the oxygen concentration is 15.5% and the intake pipe pressure is 85 kPa).

As described above, when determining the fuel property, the frequency of the determination is increased by degrading the combustion state before the performing the determination (it is obvious that the determination is performable when the combustion state is poor, but even when the combustion state is good, the determination also becomes performable by degrading the combustion state). Further, the determination accuracy is improved by causing a great combustion variation based on the retarding of the fuel injection timing. Note that it is difficult to improve the combustion state from the degraded state, and also improving the combustion state causes the combustion variation due to the retarding of the fuel injection timing to be small, which is not preferable in improving the determination accuracy.

Although the embodiment is described above, the present disclosure is not limited to this embodiment and suitable changes may be applied within the scope of the claims. Examples of such changes are described next. The number of cylinders of the engine 1 is not limited and it may be, for example, six. The number of cylinders in which the fuel injection timing is continuously retarded may be only one cylinder or three or more cylinders. The suspension period from the previous to the next retarding of the fuel injection timing is suitably settable, or it may be eliminated. As the combustion control amount which is changed according to the fuel property, without limiting to the fuel injection timing, a suitable parameter related to combustibility, such as EGR amount, may be selected. As for the combustion variation when the fuel injection timing is retarded, without limiting it to the reduction amount of the engine speed, a suitable parameter, such as angular speed variation in the engine speed, combustion pressure, combustion temperature, exhaust gas temperature, exhaust gas pressure, etc. may be selected. The application of the present disclosure is not limited to the diesel engine, but may similarly be to gasoline engines. In this case, the fuel property may be an octane number and the combustion control amount may be ignition timing, for example. If the determination at Q11 in FIG. 4 is YES, without proceeding to Q12, at another step (process), the fuel property may be determined to be intermediate and the combustion control amount may be determined based on this determination result (the determination result of the fuel property indicates a grade between the determination result of Q12 and the determination result of Q13). Each step or a group of two or more steps illustrated in the flowchart indicates a function of the controller U, and it may be understood as a component of the controller U by adding "module" to the name indicating the function. The controller U may also be referred to as the fuel property determining device and the combustion control device.

The present disclosure is suitably applicable to automobile diesel engines, etc.

It should be understood that the embodiments herein are illustrative and not restrictive, since the scope of the invention is defined by the appended claims rather than by the description preceding them, and all changes that fall within metes and bounds of the claims, or equivalence of such metes and bounds thereof, are therefore intended to be embraced by the claims.

DESCRIPTION OF REFERENCE CHARACTERS

U Controller
1 Engine
2 Cylinder
10 Fuel Injector
20 Intake Passage
22 First Exhaust Turbocharger
23 Second Exhaust Turbocharger
30 Exhaust Passage
50 EGR Passage
51 EGR Cooler
52 EGR Valve

What is claimed is:
1. A fuel injection control device for an engine, the device comprising:
an injector configured to inject fuel into a cylinder of the engine;
a throttle valve; and
a processor configured to, before retarding a fuel injection timing, control the throttle valve to narrow an opening of the throttle valve to reduce an intake air pressure to a given intake air pressure range and thereby degrade a combustion state, then control the injector to retard the fuel injection timing when the intake air pressure is within the given intake air pressure range, and determine a fuel property based on a combustion variation of the engine caused by the retarding of the fuel injection timing, wherein
the fuel property is determined while the engine is idling.

2. The device of claim 1, wherein the combustion state is degraded by increasing an exhaust gas recirculation (EGR) amount before retarding the fuel injection timing.

3. The device of claim 1, wherein an external load on the engine is reduced before retarding the fuel injection timing and before the throttle valve is controlled to narrow the opening of the throttle valve to reduce the intake air pressure to the given intake air pressure range and thereby degrade the combustion state.

4. The device of claim 1, wherein the combustion state is degraded after the combustion state becomes stable.

5. The device of claim 1, wherein the combustion variation is a variation in an engine speed when the fuel injection timing is retarded.

6. The device of claim 1, wherein a cetane number is determined as the fuel property.

7. A combustion control device for an engine, the device comprising:

an injector configured to inject fuel into a cylinder of the engine;

a throttle valve; and a processor configured to, before retarding a fuel injection timing, control the throttle valve to narrow an opening of the throttle valve to reduce an intake air pressure to a given intake air pressure range and thereby degrade a combustion state, then control the injector to retard the fuel injection timing when the intake air pressure is within the given intake air pressure range, and determine a combustion control amount of the engine in a normal operating state based on a combustion variation of the engine caused by the retarding of the fuel injection timing, wherein the combustion control amount of the engine is the fuel injection timing.

* * * * *